(12) United States Patent
Schmidt

(10) Patent No.: US 11,725,154 B2
(45) Date of Patent: Aug. 15, 2023

(54) HYDROCARBON GAS RECOVERY METHODS

(71) Applicant: Energy and Environmental Research Center Foundation, Grand Forks, ND (US)

(72) Inventor: Darren Schmidt, Williston, ND (US)

(73) Assignee: Energy and Environmental Research Center Foundation, Grand Forks, ND (US)

( * ) Notice: Subject to any disclaimer, the term of this patent is extended or adjusted under 35 U.S.C. 154(b) by 0 days.

(21) Appl. No.: 17/806,004

(22) Filed: Jun. 8, 2022

(65) Prior Publication Data
US 2022/0298438 A1    Sep. 22, 2022

Related U.S. Application Data

(63) Continuation of application No. PCT/US2021/038335, filed on Jun. 22, 2021.

(30) Foreign Application Priority Data

Jun. 22, 2020  (GB) ................................. 2009516

(51) Int. Cl.
    *C10G 5/06*     (2006.01)
    *C10G 70/04*    (2006.01)
    *C10L 3/10*     (2006.01)

(52) U.S. Cl.
    CPC ............ *C10G 70/043* (2013.01); *C10G 5/06* (2013.01); *C10L 3/103* (2013.01); *C10L 3/106* (2013.01);
    (Continued)

(58) Field of Classification Search
    CPC ..... C10G 5/06; C10G 70/043; C10L 2290/58; C10L 2290/60
    See application file for complete search history.

(56) References Cited

U.S. PATENT DOCUMENTS

| | | | | |
|---|---|---|---|---|
| 3,778,239 A | * | 12/1973 | Gambs | ...................... C10L 3/00 48/213 |
| 4,209,305 A | * | 6/1980 | Conway | .................. C01B 3/382 48/213 |

(Continued)

FOREIGN PATENT DOCUMENTS

| | | |
|---|---|---|
| CN | 205011720 U | 2/2016 |
| GB | 2582815 A | 10/2020 |

(Continued)

OTHER PUBLICATIONS

"Crude Oil Stabilization and Recovery", Aspen Engineering Services, LLC, [Online] Retrieved from the Internet: <URL: https://aspenesco.com/uploads/3/4/8/5/34851592/cosr_brochure_--_aspen.pdf>, (2018), 1 pg.

(Continued)

*Primary Examiner* — Ellen M McAvoy
*Assistant Examiner* — Ming Cheung Po
(74) *Attorney, Agent, or Firm* — Schwegman Lundberg & Woessner, P.A.

(57) ABSTRACT

A method of recovery of rich gas where the rich gas is a hydrocarbon gas comprising less than 50 mole % methane is disclosed. The method comprises the steps of gathering the low pressure gas, compressing the gathered gas, cooling the compressed gas in a condenser so that a portion of the compressed gas condenses to form a liquefied gas and liquefied gas vapour in the condenser, and discharging the liquefied gas and liquefied gas vapour from the condenser, in which the cooling of the compressed gas is performed using at least one heat exchanger (40).

20 Claims, 2 Drawing Sheets

Figure 1:
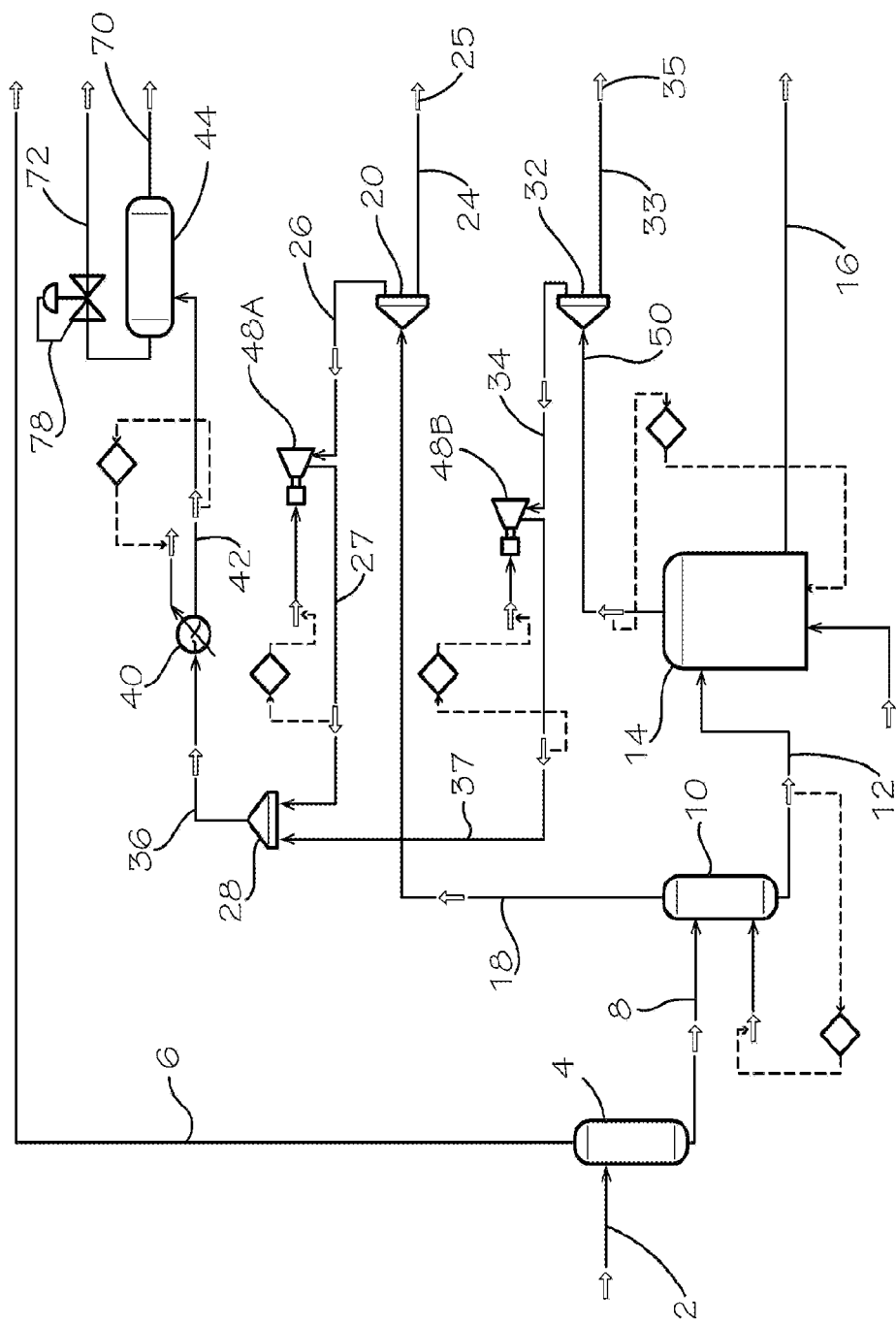

(52) U.S. Cl.
CPC .. *C10G 2300/1037* (2013.01); *C10L 2290/06* (2013.01); *C10L 2290/46* (2013.01); *C10L 2290/48* (2013.01); *C10L 2290/58* (2013.01); *C10L 2290/60* (2013.01)

(56) References Cited

U.S. PATENT DOCUMENTS

| | | | | |
|---|---|---|---|---|
| 4,320,802 | A | * | 3/1982 | Garbo ................ E21B 43/00 |
| | | | | 166/266 |
| 4,576,005 | A | | 3/1986 | Force |
| 9,581,385 | B2 | | 2/2017 | Malik |
| 9,758,735 | B2 | | 9/2017 | Meyer |
| 9,988,581 | B2 | | 6/2018 | Meyer |
| 10,017,701 | B2 | | 7/2018 | Meyer |
| 2006/0000234 | A1 | | 1/2006 | Cuellar et al. |
| 2009/0282865 | A1 | | 11/2009 | Martinez et al. |
| 2015/0233634 | A1 | * | 8/2015 | Zubrin ................ H04W 76/10 |
| | | | | 62/619 |
| 2016/0326446 | A1 | * | 11/2016 | Lokhandwala ...... C10G 70/045 |
| 2019/0128600 | A1 | | 5/2019 | Yamamori et al. |

FOREIGN PATENT DOCUMENTS

| | | |
|---|---|---|
| WO | WO-2006031362 A1 | 3/2006 |
| WO | WO-2021262624 A2 | 12/2021 |
| WO | WO-2021262624 A3 | 2/2022 |

OTHER PUBLICATIONS

"International Application Serial No. PCT/US2021/038335, International Search Report dated Sep. 17, 2021", 3 pgs.

"International Application Serial No. PCT/US2021/038335, Written Opinion dated Sep. 17, 2021", 6 pgs.

"United Kingdom Application Serial No. 2009516.2, Combined Search and Examination Report dated Dec. 11, 2020", 4 pgs.

"United Kingdom Application Serial No. 2009516.2, Response filed Aug. 19, 2022 to Combined Search and Examination Report dated Dec. 11, 2020", 10 pgs.

"International Application Serial No. PCT US2021 038335, International Preliminary Report on Patentability dated Jan. 5, 2023", 7 pgs.

* cited by examiner

HYDROCARBON GAS RECOVERY METHODS

CROSS-REFERENCE TO RELATED APPLICATIONS

This application claims priority to, and is a continuation of PCT Patent Application No. PCT/US2021/038335, filed on Jun. 22, 2021, which claimed priority to GB Patent Application No. 2009516.2, filed on Jun. 22, 2020, which applications are incorporated herein by reference in their entirety.

This invention relates to hydrocarbon gas recovery methods and, in particular, to the recovery of hydrocarbon gas that is emitted during the extraction and treatment of crude oil which would otherwise be vented or flared.

Hydrocarbon gases are almost always associated with crude oil in an oil reserve, because they represent the lighter chemical fraction (shorter molecular chain) formed when organic remains are converted into hydrocarbons. Such hydrocarbon gases may exist separately from the crude oil in the underground formation or they may be dissolved in the crude oil. As the crude oil is extracted from the reservoir and raised to the surface or subsequent to that process, the pressure in the crude oil is reduced to atmospheric pressure and dissolved hydrocarbon gases come out of solution. Such gases occurring in combination with the crude oil are often referred to as "associated" gas.

At well pads where the production of oil and associated gas is of high volume and high pressure, so called high producing well pads, it is economic to use existing technologies to separate the associated gas from the oil to produce what may be called "sales" gas and to process the sales gas. The processing of the sales gas can produce pipeline quality natural gas and some purity products in the form of propane, butane, and gas condensate. The natural gas is introduced into a gas pipeline or a storage means for onward transmission and or sale, and the purity products are generally sold and or stored separately. The sales gas generally comprises around 50% methane ($CH_4$), 20% ethane ($C_2H_6$), 13% propane ($C_3H_8$), 5% butane ($C_4H_{10}$), and the balance is heaver hydrocarbons.

At well pads where the production of oil and associated gas is of not of high volume or high pressure, so called low producing well pads, it may not be economic to install and use existing technologies to process the sales gas in the same way that it is processed at high producing well pads. At such well pads, any gas that comes out of the oil may be treated as "flare" gas.

Once the crude oil has been extracted from the ground, it is generally passed through a 2 phase separator with the intention of separating the sales gas from the oil. Thereafter the oil may undergo other processes, for example passing that oil through heater treater apparatus and/or storage in a storage tank. Associated gasses are given off by the oil during those other processes. Those gasses are at low pressure and generally contain little to no methane and the majority of the gas is a mixture of ethane, propane and butane. This gas may be called rich gas because it is rich in ethane, propane and butane. For the purposes of this invention rich gas is defined as a hydrocarbon gas with a gas composition comprising less than 50 mole % methane. These gasses are also often known as "flare" gases. Again it is not economical to process this rich gas in the same fashion as the sales gas is processed.

Historically rich gas has been considered to be a by-product or waste product of oil production and this gas has been typically disposed of by venting or flaring (burning) that gas. Venting and flaring are relatively inexpensive ways to deal with rich gas, but result in relatively high emissions (e.g., large quantities of greenhouse gases) and fail to capture any of the energy contained within the gas.

Improved flaring systems and methods have been developed to reduce flare emissions sufficiently to satisfy stringent emission standards, however, many of these improved flaring systems merely convert the energy within the flare gas into thermal energy which releases to the environment. These improved flaring systems do not capture the energy contained within the flare gas.

Any flaring system is, in addition to its criteria pollutants, going to contribute to carbon dioxide emissions (carbon footprint) generated by the operator of the flare. There is ever increasing pressure on oil field operators to reduce and minimise their carbon footprint.

Other gas utilization techniques such as bi-fueling diesel engines or frac water heating have been tried, but those techniques have been found to be challenged with marginal economics and rely on niche applications and/or a large volume throughput.

According to a first aspect of the present invention there is provided a method of recovery of rich gas where the rich gas is a hydrocarbon gas comprising less than 50 mole % methane comprising the steps of
gathering the low pressure gas,
compressing the gathered gas,
cooling the compressed gas in a condenser so that a portion of the compressed gas condenses to form a liquefied gas and liquefied gas vapour in the condenser, and
discharging the liquefied gas and liquefied gas vapour from the condenser,
in which the cooling of the compressed gas is performed using at least one heat exchanger. The liquefied gas and liquefied gas vapour is discharged into one or more storage means, for example storage tanks.

The rich gas may have the further characteristic that it has a gauge pressure of less than or equal to 1379.0 kPa (200 psi), 689.5 kPa (100 psi), or 344.7 kPa (50 psi).

The benefit of using at least one heat exchanger to cool the compressed gas and, as a result, cause it to condense is that heat exchangers are a simple and well established technology. This results in their being relatively inexpensive, reliable, and easy to maintain. A further benefit is that the heat exchanger can be relatively small and as such can be operated (both in terms of operational conditions and in terms of the economics of operation) in situations where the volume of the compressed gas will not be large, for example less than 1 $m^3$. This ability to operate on a small scale has the benefit that the method of the present invention can be deployed at well pads and other places where the rich (flare) gas or mixture of rich (flare) and sales gasses are generated in small volumes.

The ability of the method and apparatus of the present invention to operate economically in connection with rich gas that is generated at small volume is advantageous. This is because although any one such location is likely to give rise to only a relatively small volume of gas, failure to recover that small volume of gas at a large number of such locations (for example, one or more oil fields which have a large number of well pads that each generate a small volume of flare gas) will lead to a large cumulative volume of non-recovered rich gas. That large volume would, if flared, represent a large contribution to the oil field or operator's carbon footprint and associated emissions. The method and apparatus of the present invention thus provides a method of reducing the volume of flared gas at locations of crude oil production and at oil producing facilities.

In some embodiments of the present invention, the heat exchanger is a fan-cooled condenser. In some embodiments, the heat exchanger is electrically powered. In some embodiments the electricity powering the heat exchanger is generated by a generator powered by burning a portion of the gathered rich gas.

The rich gas may be gathered from one or more of a 2-phase separator, a treater unit, a vapour recovery tower, and an oil storage tank. Alternatively, the rich gas may be gathered from other sources.

The step of compressing the rich gas may be performed using one or more gas compressors such as compression pumps suitable for the compression of gas. The input to each gas compressor is in fluid connection with at least one source for gathering the rich gas. The output from each gas compressor is in fluid communication with the condenser and storage tank.

The rich gas gathered from each source may be compressed by a gas compressor dedicated to that source.

One or more of the gas compressors may be an oilless compression pump.

One or more of the gas compressors may be a variable speed compression pump.

One or more of the gas compressors may operate continuously and the gas compressor may be configured to continuously compress a small flow rate of gas, for example around 0.2 m$^3$ (7 cubic feet) of gas per minute. In some examples the volume of gas to be compressed may be in the range of 0.001 to 1.000 m$^3$ per minute.

In some embodiments of the present invention, the or each gas compressor is controlled by a control unit, and the control unit comprises a central processing unit and at least one pressure sensor adapted to measure the pressure of the incoming gas at the or each gas compressor. In some alternative embodiments, the or each gas compressor is controlled by a control unit, and the control unit comprises a central processing unit and at least one pressure sensor adapted to measure the pressure of the rich gas at the or each source of such gas (the source pressure(s)), and the control unit may shut off a gas compressor if the source pressure associated with that gas compressor falls below a predetermined minimum pressure.

In some embodiments, a central processing unit controls each gas compressor via an on/off switch or a variable speed controller. In some embodiments the central processing unit varies the speed of each gas compressor dependent on a source pressure measurement. In some embodiments when the pressure of the compressed gas is at or above a predetermined pressure the or each gas compressor is stopped. In some embodiments the pressure of the liquefied gas and vapour discharged from the condenser is measured and the central processing unit stops the or each gas compressor if a predetermined pressure is exceeded.

It is known that for hydrocarbon gases, including rich gasses, there is a temperature, known as the dew point temperature, at which the gas starts to condense and form a liquid. One of the factors which determines the dew point temperature for a given gas, for example flare gas, is the pressure of the gas. It is the case that the higher the pressure of the gas, the higher the dew point temperature for the gas. For example, for a hydrocarbon gas at an absolute gas pressure of around 2068 kPa (300 psia) the dew point temperature for that gas may be around −35 degrees Centigrade (−32 degrees Fahrenheit), whereas at an absolute gas pressure of around 4020 kPa (583 psia) the dew point temperature for that gas may be around 16 degrees Centigrade (60 degrees Fahrenheit).

A further factor that will determine the dew point of a hydrocarbon gas is the composition of the gas. It has been found that the greater the amount of methane in the gas the lower the dew point temperature of the gas. It has been found that for hydrocarbon gases with a composition that includes more than 50 mole % methane the dew point of the gas is at very low or cryogenic temperatures (less than −150 degrees Centigrade (−238 degrees Fahrenheit).

When the rich gas is compressed by the or each gas compressor the temperature of the gas increases, for example the temperature of the compressed gas may rise to around 150 degrees Centigrade (300 degrees Fahrenheit). That hot compressed gas is pumped toward the condenser. In examples of the invention in which there are two or more sources of the rich gas, the flows of hot compressed gas are merged in the condenser or before the flows of gas reach the condenser.

When the gas passes into the condenser, it may be cooled by the heat exchanger to a temperature of between about −18 to 27 degrees Centigrade (0 to 85 degrees Fahrenheit). Each compression pump runs to maintain a compressed gas gauge pressure of around 1724 kPa (250 psi), or in the range of 1379 to 2068 kPa (200 to 300 psi) or 1551 to 1896 kPa (225 to 275 psi) in the condenser and each storage means. At these temperatures and pressures at least a portion of the compressed gas will condense in the condenser.

The condensate or liquefied gas formed in the condenser is a liquid comprising one or more hydrocarbons such as ethane, propane and butane. The liquefied gas and liquefied gas vapours may pass out of an exit of the condenser, possibly in combination with some non-condensed gas. In some examples of the present invention the sizing of the exit from the condenser determines the rate of flow of the liquefied gas and vapour out of the condenser.

In some examples of the present invention when the heat exchange is a fan-cooled condenser the fan is constantly running. The operation of the fan-condenser may be independent of the operation of the or each compression pump and/or independent of the pressure in the condenser.

In some embodiments of the present invention the liquefied gas, liquefied gas vapour and any non-condensed gas passes from the condenser into one or more storage tanks. Each storage tank may be so constructed that it can hold the liquefied gas, any associated vapour and non-condensed gas at a gauge pressure of about pressure of about 1724 kPa (250 psi) or in the range of 1379 to 2068 kPa (200 to 300 psi) 011551 to 1896 kPa (225 to 275 psi) within an expected range of temperatures. That expected range of temperatures may be the expected range of ambient temperatures at the location of each storage tank.

The storage tank may be fitted with a back pressure regulator to maintain that pressure of about 1724 kPa (250 psi) or in the range of 1379 to 2068 kPa (200 to 300 psi) or 1551 to 1896 kPa (225 to 275 psi) within an expected range of temperatures.

In some examples of the present invention each storage tank comprises a level sensing means. That level sensing means may be in communication with a control unit for each compression pump. The control means may stop each compression pump if a predetermined level is reached in the storage tank.

In embodiments where there are more than one storage tank, the control means may additionally or alternatively be able to actuate a valve at the entry to a storage tank or between the condenser exit and the storage tank that prevents or allows the flow of liquefied gas and liquefied gas vapour and any non-condensed gas into the tank.

In some examples, the level sensing means may be in communication with a remote location, for example via the internet or other communications network, so that the operator of the well pad at which the method of the present invention is being performed may know when the or each storage tank needs to be emptied.

The non-condensed gas exiting the condenser will, in terms of volume, energy, and/or carbon content be significantly smaller than the rich gas. The non-condensed gas may be expected to comprise a higher proportion of methane than the rich gas. It may be vented from the storage tank and introduced to a source of the rich gas, compressed and introduced to a flow of rich gas from a compression pump to the condenser, used to generate electricity via a gas burning generator, flared or disposed of in some other fashion.

In some examples of the present invention the or each compression pump may be controlled by a control unit. The control unit may comprise a central processing unit and a memory. The memory may comprise a table containing desired operating parameters for the method of the present invention including but not limited to minimum rich gas pressures at the sources of rich gas, minimum and maximum pressures (in the liquefied gas vapour or the liquefied gas) in the or each storage means. The control unit may further comprise the sensors necessary to gather the data that the central processing unit requires to utilise the table in the memory.

The method of the present invention may further comprise a step of removing at least a portion of any sulphur, oxygen, and water present in the rich gas before the condensing step. Including this step in the method of the present invention has the advantage that it will remove at least some of the undesirable impurities of sulphur, oxygen, and water from the liquefied gas which is stored in the or each storage means. This step will also minimise the volume of the liquefied gas and thus maximise the amount of useful liquefied gas that can be stored in the or each storage means. A known gas cleanser may be used to remove the at least a portion of any sulphur, oxygen, and water in the gas.

The at least one storage means may be a single storage tank of sufficient size that it can store a known number of days, weeks or months production of liquefied gas. When such a storage tank is sufficiently full, a transportation means, such as a road tanker, can visit the storage tank and draw some or all of the contents of the storage tank into the transport means. The liquid gas may then be transported to a location suitable for further processing of the liquid gas. Such transportation means are often configured to transport liquid gasses at a pressure of around 1724 kPa (250 psi) at ambient temperature. It is thus an advantage of the present invention that the liquefied gas produced by the method of the invention may be at that pressure and temperature because it makes the transfer of the liquefied gas into the transportation means relatively simple According to a second aspect of the present invention there is provided an apparatus suitable for liquefying and storing rich gas where the rich gas is a hydrocarbon gas comprising less than 50 mole % methane comprising a means for gathering rich gas, at least one means for compressing the gathered gas, a means for condensing the compressed gas to form a liquefied gas, and at least one storage means, in which the condensing of the compressed gas is performed using at least one heat exchanger. The advantages of the apparatus of the second aspect of the present invention are as discussed in connection with the method of the first aspect of the present invention.

The at least one heat exchanger may be a fan-cooled condenser.

The means for gathering the rich gas may comprise one or more conduits providing fluid communication between a source of the rich gas and at least one compressor means.

The means for compressing the rich gas may be a gas compressor such as a gas compression pump.

In some embodiments of the present invention, each gas compressor is associated with a control unit and conduit means fluidly linking the output from the gas compressor to the heat exchange and a storage means, in which the control unit comprises a central processor unit and at least one pressure sensor adapted to measure the pressure of the rich gas at its source. The control unit may comprise further pressure sensors to measure the pressure of the compressed gas between the or each gas compressor and the heat exchanger, and/or the liquefied gas after it has passed through the heat exchanger. The liquefied gas pressure may be measured in the storage tank. The gas compressor may be speed controlled with input from the rich gas source pressure measurement. The control unit may switch each gas compressor off when the pressure of the compressed gas between the or each gas compressor and the heat exchanger, and/or the pressure of the liquefied gas is at or above a predetermined pressure and or the source pressure of the rich gas is below a predetermined pressure. A single control unit may control more than one gas compressor.

The control unit may comprise a central processing unit, a memory, at least one pressure sensor adapted to source pressure of the rich gas, and at least one pressure sensor adapted to measure the pressure of the liquefied gas in the storage unit.

According to a third aspect of the present invention there is provided a computer program product comprising computer readable instructions that, when run on a computer, is configured to cause a processer to perform the method of the first aspect of the present invention.

A computer program product may be provided for controlling at least one gas compressor, the computer program product comprising computer readable instructions that, when run on one or more computers, are configured to cause one or more processers to determine the gas or liquefied gas pressures at different positions in the apparatus of the present invention, and to control the operation of the gas compressors to keep the measured pressures within predetermined parameters.

The apparatus may further comprise a gas cleaner suitable for removing at least a portion of any sulphur, oxygen, and water from the gas.

In some embodiments of the present invention, the at least one storage means is a storage tank.

Figure 2:
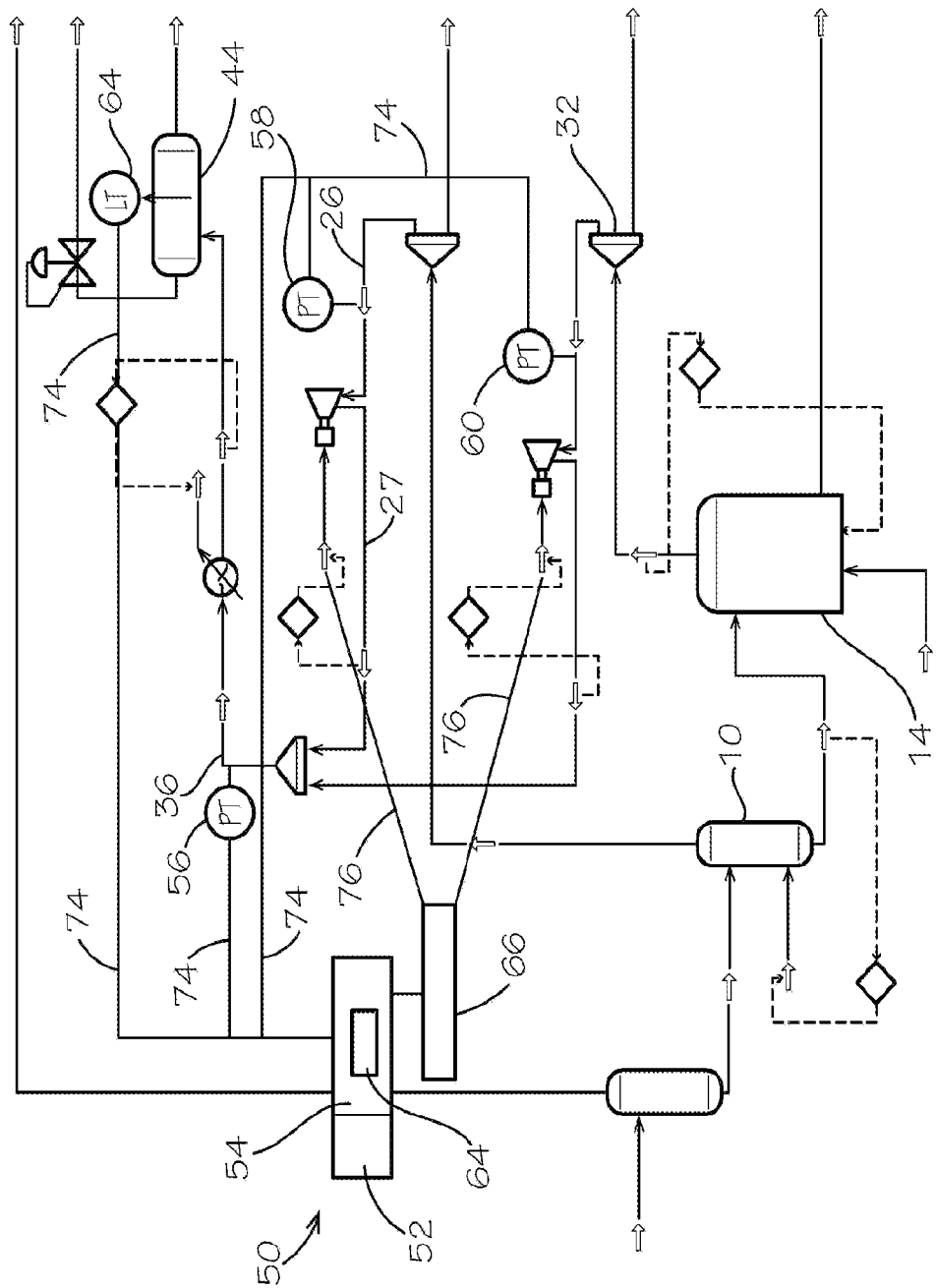

The present invention will be further described and explained by way of example and with reference to the drawings in which:

FIG. 1 shows a schematic embodiment of an apparatus according to the present invention operated by the method of the present invention; and FIG. 2 shows an the schematic view of FIG. 1 including a control unit.

FIG. 1 shows a schematic view of a well pad. In which a flow of crude oil 2 is introduced into a 2-phase separator 4. In the 2-phase separator 4 sales gas separates from the oil and is drawn off via a conduit 6. The sales gas is treated and introduced to a gas pipeline by means not shown.

The oil that has passed through the 2-phase separator 4 flows along a conduit 8 to a heater treater 10. After treatment in the heater treater 10 the treated oil flows along a conduit 12 to a storage tank 14. The oil is stored in the tank 14 until it is drained from the tank 14 via the conduit 16 and transported elsewhere.

Whilst the oil is being treated in the heater treater 10 and sitting in the storage tank 14 rich gas will come out of solution and collect in gas phase in the heater treater 10 and storage tank 14. The rich gas is removed from the heater treater 10 via the conduit 18 to a divergent two-way junction 20 which includes a means (not shown) to direct the gas into one or both of first and second exiting conduits 24, 26.

The first conduit 24 exits the junction 20 and is in communication with a high pressure flare 25.

The second conduit 26 allows the gas from the heater treater 10 to flow to a compression pump 48A in which it is compressed. The compressed gas flows from the compression pump 48A along a conduit 27 to a convergent two-way junction 28.

In the storage tank 14 rich gas builds up and, when released, flows to a divergent two way junction 32 via a conduit 30. Divergent two way junction 32 includes a means (not shown) to direct the gas into one or both of first and second exiting conduits 33, 34.

The first conduit 33 exits the junction 32 and is in communication with a low pressure flare 35.

The second conduit 34 allows the gas from the storage tank 14 to flow to a compression pump 48B in which it is compressed. The compressed gas flows from the compression pump 48B along a conduit 37 to the convergent two-way junction 28.

Both of the compression pumps 48A and 48B are configured to compress the rich gas to a gauge pressure of about 1724 kPa (250 psi) or in the range of 1379 to 2068 kPa (200 to 300 psi) or 1551 to 1896 kPa (225 to 275 psi). When the rich gas is compressed by either of the compression pumps 48A and 48B it increases in temperature, typically to around 150 degrees Centigrade (300 degrees Fahrenheit). At the convergent two-way junction 28 the gas flowing along conduits 27 and 37 merges and the compressed gas flows along the conduit 36 to a heat exchange 40 which is a fan-cooled condenser unit.

The heat exchange 40 cools the pressurised gas to a temperature that is about equal to the ambient temperature around the heat exchange 40. With the cooling of the gas liquefied gas condenses out of the gas. The pressure of the compressed gas is maintained within the heat exchange 40 by the pumping action of one or both of compression pumps 48A and 48B which compensates for any potential pressure drop due to cooling of the compressed gas and/or the condensation of liquefied gas.

The liquefied gas and liquefied gas vapour exits the heat exchange 40 via a conduit 42. The liquefied gas and liquefied gas vapour then enters a storage tank 44 and is held in that tank until that tank is emptied into a transportation means (not shown) via a drain means (70).

The conduit 72 exiting the storage tank 44 is provided with a back pressure control valve 78 set at 1724 kPa (250 psi). This maintains a pressure of 1724 kPa (250 psi) in the storage tank but allows gas/vapour/liquid gas to vent through conduit 72 to relieve excess pressure in the storage tank 44.

With reference to FIG. 2 and with continued reference to FIG. 1, the gas pressure within the storage tank 40 is determined and controlled by a control unit 50 for the compression pumps 48A and 48B.

The control unit 50 comprises a central processing unit 52, a memory 54, a pressure sensor 56 adapted to measure the pressure of the compressed gas in the conduit 36, a pressure sensor 58 adapted to measure the rich gas pressure in the conduit 26 which carries rich gas from the heater treater 10, a pressure sensor 60 adapted to measure the rich gas pressure in the conduit 34 which carries rich gas from the storage tank 14, and a level sensor 64 adapted to measure the level of the liquefied gas in the storage tank 44. The gas pressure in the conduits 26 and 34 is the pressure of the rich gas as it exits the heater treater 10 and storage tank 14 respectively.

Each of the sensors 56, 58, 60, and 62 are in data communication with the central processing unit 52 via one or more known data communication means 74. For example, but without limitation, data communication means 74 may be electrical wires, or via wireless networking.

The memory 54 of the control unit 50 comprises a table 64 relating to the desired operating parameters of the apparatus, for example, minimum pressure readings in conduits 26 and 34, a maximum pressure in the conduit 36, and the maximum liquid level in the storage tank 44.

The central processing unit 52 uses the table 64 and input signals (representative of data) from the sensors 56, 58, 60, and 62 to determine whether none, one, or both of the compression pumps 48A and 48B should be running. The compression pumps 48A and 48B are controlled by a variable speed switch 66 which communicates control signals to the compression pumps 48A, 48B via data communication means 76. For example, but without limitation, data communication means 76 may be electrical wires, or via wireless networking.

The central processing unit 52 may further use the table 64 to determine whether a warning that the storage tank 44 is approaching its predetermined maximum capacity for liquefied gas, or the storage tank 44 has reached maximum capacity. The warning can be issued locally to the control unit 50, at one or more locations remote from the control unit 50 or both. If the maximum capacity of the storage tank 44 has been reached the variable speed switch 66 may switch of the compression pumps 48A, 48B.

If there are any gasses that pass into the storage tank 44 which do not liquefy, those gasses may flow through a conduit 72 to a flare stack where that remaining gas can be flared. The volume of that gas, and hence the carbon footprint associated with that flaring is substantially lower than would have been the case if the rich gas were flared without being treated according to the method of the present invention. Alternatively, conduit 72 may be routed so that it feeds those gasses back into conduit 36.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the method and apparatus disclosed in the various embodiments, examples and drawings of this disclosure may be used alone, in combination, or in a variety of arrangements not specifically discussed in the embodiments, examples and drawings described above. This disclosure is therefore not limited in its application to the details and arrangement of components set forth in the above description or illustrated in the drawings. For example, aspects described in one embodiment may be combined in any manner with aspects described in other embodiments.

Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method of recovery of rich gas, the method comprising:
flowing crude oil to a 2-phase separator to form a sales gas stream and a liquid hydrocarbon stream;
flowing the liquid hydrocarbon stream to a heater treater to form a first rich gas composition comprising less than 50 mol % methane and an oil stream;
flowing the oil stream to an oil storage tank, the oil storage tank comprising a second rich gas composition in a headspace thereof comprising less than 50 mol % methane;
compressing the first rich gas composition and the second rich gas composition;
cooling the compressed first rich gas composition and the compressed second rich gas composition in one or more condensers so that a portion thereof condenses to form a liquefied gas and liquefied gas vapor in the condenser; and
discharging the liquefied gas and liquefied gas vapor from the condenser.

2. The method of claim 1, wherein the first and second rich gas composition have a gauge pressure of less than or equal to 1379.0 kPa (200 psi).

3. The method of claim 1, wherein the liquefied gas and liquefied gas vapor is discharged into one or more storage means.

4. The method of claim 3, wherein the at least one storage means is a storage tank.

5. The method of claim 1, wherein the condenser is a fan-cooled condenser.

6. The method of claim 1, wherein the first and/or second rich gas composition is gathered from one of more additional sources, the one or more additional sources being selected from a two-phase separator and a vapor recovery tower.

7. The method of claim 1, wherein the step of compressing the gas is performed using at least one compression pump.

8. The method of claim 7, wherein:
each compression pump is controlled by a control unit,
the control unit comprises a central processor unit and at least one pressure sensor adapted to measure a source pressure,
the source pressure is the pressure of the first or second rich gas composition at a source of such gas, and
the central processor unit turns off each compression pump associated with that source when the source pressure is at or below a predetermined pressure.

9. The method of claim 1, wherein the compressing of the first and second rich gas composition comprises compressing the first and second rich gas composition to a gauge pressure of in the range of 1379 to 2068 kPa (200 to 300 psi).

10. The method of claim 1, wherein the method further comprises removing at least a portion of any sulfur, oxygen, and water from the first and/or second rich gas composition before the condensing step.

11. The method of claim 10, wherein the at least a portion of any sulfur, oxygen, and water in the gas is removed by passing the gas through a gas cleaner.

12. The method of claim 1, wherein the method is a method of reducing the amount of gas flared from a well pad or an oil production facility.

13. The method of claim 1, wherein the method is a computer-implemented method.

14. The method of claim 1, further comprising discharging non-condensed gas from the condenser.

15. The method of claim 14, wherein the non-condensed gas comprises a higher proportion of methane than the first and second rich gas composition.

16. The method of claim 14, further comprising adding the non-condensed gas to a storage tank.

17. The method of claim 14, further comprising introducing the non-condensed gas to a source of the first and/or second rich gas composition.

18. The method of claim 14, further comprising compressing the non-condensed gas and adding the compressed product thereof to the compressed gas that is cooled in the condenser.

19. The method of claim 14, further comprising burning the non-condensed gas and generating electricity therefrom.

20. The method of claim 1, further comprising introducing the sales gas, natural gas formed therefrom, and/or a purified product of the sales gas into a stream of commerce.

* * * * *